United States Patent [19]

Swann

[11] Patent Number: 5,009,743
[45] Date of Patent: Apr. 23, 1991

[54] CHEMICALLY-ASSISTED ION BEAM MILLING SYSTEM FOR THE PREPARATION OF TRANSMISSION ELECTRON MICROSCOPE SPECIMENS

[75] Inventor: Peter R. Swann, Diablo, Calif.

[73] Assignee: Gatan Incorporated, Pleasanton, Calif.

[21] Appl. No.: 431,401

[22] Filed: Nov. 6, 1989

[51] Int. Cl.$^5$ .............. H01L 21/306; B44C 1/22; C03C 15/00; C03C 25/06
[52] U.S. Cl. .................... 156/643; 156/646; 156/654; 156/662; 156/345; 204/192.34; 204/192.35; 204/298.36
[58] Field of Search ............. 156/643, 646, 654, 655, 156/656, 657, 662, 345; 204/192.34, 192.35, 192.37, 298.36; 219/121.33, 121.51, 121.55, 121.84; 250/492.1, 492.2, 492.3

[56] References Cited

U.S. PATENT DOCUMENTS

| | | | |
|---|---|---|---|
| 4,734,152 | 3/1988 | Geis et al. | 156/646 |
| 4,734,158 | 3/1988 | Gillis | 204/298 BE |
| 4,874,459 | 10/1989 | Coldren et al. | 156/643 |
| 4,874,460 | 10/1989 | Nakagawa et al. | 156/627 X |

FOREIGN PATENT DOCUMENTS 2145360 3/1985 United Kingdom .

Primary Examiner—William A. Powell

[57] ABSTRACT

An ion beam milling system for the preparation of transmission electron microscope specimens suitable for atomic resolution imaging, particularly of III-V and II-VI compound semiconductors and their alloys, is described. The system includes ion beam sources and reactive molecular gas jets which may be operated in combination or separately, as appropriate. A new heated specimen holder, giving greatly increased reaction rates with the molecular gas jet, allows milling angles very close to zero.

10 Claims, 1 Drawing Sheet

CHEMICALLY-ASSISTED ION BEAM MILLING SYSTEM FOR THE PREPARATION OF TRANSMISSION ELECTRON MICROSCOPE SPECIMENS

BACKGROUND—FIELD OF INVENTION

The invention relates to ion beam milling system for the preparation of transmission electron microscope specimens and particularly to variants employing reactive chemicals in addition to the usual inert gas ion source, e.g. argon.

BACKGROUND—DESCRIPTION OF PRIOR ART

Transmission electron microscopy is an important technique for studying the detailed microstructure of many materials. Recently, transmission electron microscopes (TEMs) operating at accelerating voltages of 300–400 kV having resolving capabilities better than 0.2 nm have become commercially available. Combined with advances in the design and fabrication of semiconductor electronic devices, this has stimulated considerable interest in obtaining "atomic resolution" TEM images from such devices.

The preparation of specimens for "atomic resolution" TEM is a demanding procedure and requires that the final specimen by very thin (<50 nm) and free from artifacts. The procedure typically involves sectioning, slicing, trepanning and grinding operations to produce a tin (~100-200 μm) disk of ~3 mm diameter. The disc is further processed by either wet chemical or electro-chemical polishing/jetting or ion beam milling with a collimated beam of ions and neutrals. The desired end result in either case is the production of a ~200 μm diameter hole in the specimen, the material on the periphery of which is sufficiently thin for high resolution TEM.

Chemical methods are successful for preparing specimens from homogeneous material but preferential action makes this technique unsuitable for preparing specimens from compound semiconductors and many-layered electronic devices, particularly when producing the more informative cross-sectional specimens. Ion milling, however, is more even in its erosion of the specimen and has been extensively applied to the problem.

Heretofore, commercially available ion beam milling systems have almost exclusively operated with argon and have had considerable success with devices fabricated from silicon. However, III-V and II-VI compound semiconductors and their alloys, such as indium phosphide, cadmium telluride, zinc sulphide and zinc selenide are becoming very important for the construction of advanced devices and, for these materials, argon-based ion milling systems are unsuitable because they produce numerous serious artifacts such as crystal imperfections, amorphous surface layers and, in the case of indium-containing materials, islands of metallic indium.

Several solutions to this problem have been investigated by various workers, including the use of heavy inert gases such as xenon and specimen cooling by liquid nitrogen. These approaches have had some limited success but recently reactive ion milling with iodine ion sources has resulted in significant improvements in the quality of the final specimen (Chew and Cullis. *Ultramicroscopy* 23 (1987) 175-198).

A known ion milling system, described in United Kingdom Patent GB No. 2,145,360 and commercially manufactured by ion Tech Ltd in the United Kingdom, is available with iodine ion sources. In this system, crystals of iodine are placed in a vessel which is connected to the anode of the ion gun in an evacuated specimen milling chamber. The ion guns generate a beam of iodine ions and neutrals which impinge on the specimen, progressively removing material to produce an electron transparent region. This system is moderately successful in producing specimens of sufficient quality for atomic resolution TEM. However, it uses significant quantities of iodine and the discharge within the ion guns generates a highly reactive plasma which rapidly corrodes and eventually destroys the ion guns. Consequently, the gun components need replacing at frequent intervals. Even worse, the large quantities of iodine released into the vacuum chamber cause general corrosion of the instrument and especially of the vacuum system. Finally, the exhaust from the pumps must be carefully controlled and filtered to prevent excessive release of iodine into the atmosphere.

In a second known ion milling system (originally described and claimed in patent application Ser. No. 222,470, filed Jul. 21, 1988, and since abandoned), manufactured by Gatan Inc, a similar approach is employed although careful design of the ion guns minimizes the quantities of iodine used. Even so, iodine consumption is unacceptably high and similar problems of corrosion are encountered.

Artefacts, such as dislocations and amorphous surface layers are often created during ion beam milling. These are a result of the penetration of energetic ions and neutrals into the surface of the specimen. Both effects can be minimized by arranging that the incident beam strikes the specimen surface at a very shallow angle. An angle of 15°-20° between the incident beam and specimen surface is often employed since this maximizes the sputtering effect of the beam although even shallower angles would further reduce damage. The smoothness of the specimen surface is promoted by rotating the specimen about a surface normal.

The relatively slow action of ion milling means that all known systems for TEM specimen preparation employ, in their primary configuration, two ion guns to thin the specimen simultaneously from both side to maximize the thinning rate. Some systems have special modes of operation using one or two guns to thin the specimen from one side only; these modes are employed when thinning to a specific layer in the specimen.

The requirements of low angle milling, milling from both sides and specimen rotation have resulted in a standard design of specimen holder. This comprises two thin metal (normally molybdenum or tantalum) discs with central apertures of a diameter just less than the usual specimen diameter, i.e. ~3 mm. The specimen is placed concentrically with the apertures between the discs which are then clamped together and mounted in an auxiliary holder providing rotation. Since the ions beams are collimated rather than focused, they are relatively broad compared with the specimen and in addition to striking the specimen also strike the clamping discs. This results in another troublesome artefact; material from the specimen clamping discs and auxiliary holder is sputtered onto the specimen. Further, the requirement for some mechanical strength in the specimen clamping discs imposes an upper limit on their thickness which in turn limits the minimum milling angle to ~10°.

While previous ion beam milling systems have often used specimen cooling as a method to reduce ion beam damage in the specimen, this is not appropriate with highly reactive halogen species, particularly iodine and bromine with high freezing points. Firstly, specimen cooling results in iodine condensing on to the specimen and the specimen holder. When the specimen is subsequently returned to room temperature, there is a very large, sudden release of iodine which is even more damaging and dangerous than the slow, continuous release which occurs without cooling. Secondly, iodine, bromine and other halogens act through temperature dependent chemical reactions occurring on the specimen surface and cooling actually reduces the efficiency of the process.

SUMMARY, OBJECTS AND ADVANTAGES

The present invention separates the reactive gas source from the ion guns, providing completely separate ion beam milling and molecular gas jetting. Further a new design of specimen holder permits milling angles approaching 0° with reduced specimen contamination while a specimen holder heater increases the reaction rate between the specimen and the reactive gas. Accordingly several objects and advantages of this invention are:

(a) to provide a new ion milling system for TEM specimen preparation having independent inert gas ion guns and molecular gas sources, each optimized appropriately;
(b) to significantly reduce the quantity of the reactive gas species consumed, thereby extending the useful lifetime of the ion gun components and minimizing damage all parts of the ion mill;
(c) to minimize the exhaust of corrosive substances;
(d) to permit milling angles between the ion beam and specimen surface close to zero;
(e) to minimize contamination of the specimen by sputtering from the specimen holder; and
(f) to provide increased reaction rates between the iodine, bromine, chlorine or fluorine and the specimen while maintaining the high specimen quality.

DRAWING FIGURES

DRAWING REFERENCE NUMERALS

Figure 1:
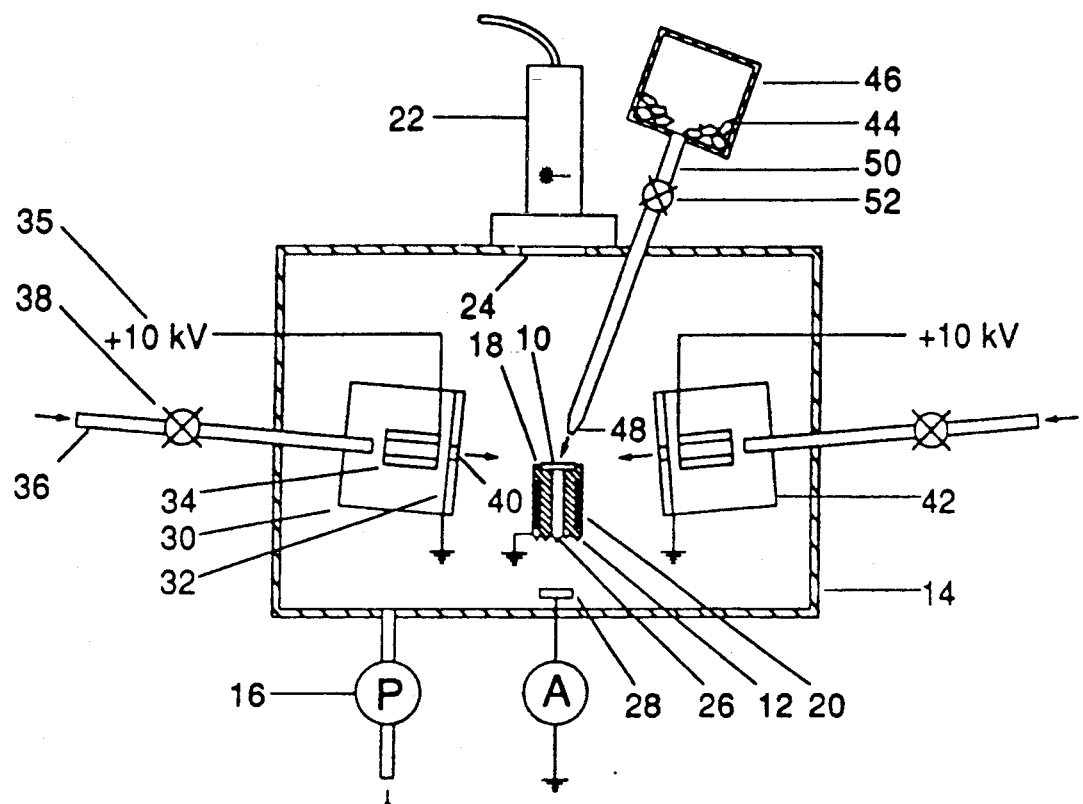
FIG. 1 illustrates the preferred embodiment of the invention.

10: specimen
12: specimen pedestal
14: vacuum chamber
16: pump
18: pedestal rim
20: heater
22: laser
26: pedestal bore
28: photodetector
30: first ion gun
32: cathode
34: anode
35: high voltage supply
36: first supply line
38: first supply valve
40: cathode aperture
42: second ion gun
44: iodine crystals
46: capsule
48: nozzle
50: second supply line
52: second supply valve.

DESCRIPTION OF THE PREFERRED EMBODIMENT

With reference to FIG. 1, specimen 10 seats on specimen pedestal 12 within vacuum chamber 14 evacuated to $\sim 10^{-6}$ Torr by pump 16. Small pedestal rim 18 of height less than the thickness of specimen 10 retains specimen 10 on the end of specimen pedestal 12. Heater 20, wrapped about specimen pedestal 12 is used to raise the temperature of the specimen. Light from laser 22, positioned directly above specimen 10, shines through window 24 on to specimen 10. Thinning may be automatically terminated on perforation of specimen 10 when light from laser 22 passes through specimen 10, down pedestal bore 26 and strikes photodetector 28.

First ion gun 30 comprises cathode 32 connected to ground and anode 34 connected to adjustable high voltage supply 35. Argon is supplied to first ion gun 30 via first supply line 36, the flow being regulated by first supply valve 38. The high voltage discharge between anode and cathode generates and directs an energetic ion beam via cathode aperture 40 towards specimen 10. Charge recombination results in the beam impinging on the specimen being composed mainly of energetic neutrals. Second ion gun 42 is constructed after a similar fashion to first ion gun 30. The two ion guns are arranged symmetrically about the specimen and so positioned that the angle between the specimen surface and the ion beams is about 5°. Although argon is typically used to generate the ion beams almost any noble gas or other inert gas is suitable. For example, krypton, xenon, nitrogen and carbon dioxide would all be possible. Ion beam induced damage in the specimen may be reduced by reducing the voltage applied to the ion guns, perhaps as low as 500 V.

Iodine crystals 44 are contained within capsule 46 mounted outside vacuum chamber 14. Capsule 46, via second supply line 50, connects to nozzle 48. The high vapor pressure of iodine at room temperature and the lower pressure within vacuum chamber 14 result in a strong flow of iodine vapor second supply line 50 to nozzle 48, directing a jet of iodine vapor on to specimen 10. Compared with the ion gun beam, the molecular gas jet is low energy. Prior art suggests that the ratio of nozzle diameter to length is critical for obtaining a well collimated jet and must be equal to 1:10. For the present invention as described, this is not found to be a very sensitive parameter. The optimum value was determined to be ~1:5 but values from 1:4 to 1:6 were almost as effective. The flow rate of iodine vapor is adjustable by second supply valve 52. Iodine crystals 44 may be replaced by bromine or other suitable material having a significant vapor pressure at room temperature or volatile liquids, such as carbon tetrachloride, in a suitable carrier.

A particular advantage of the present invention is its flexibility of operation. Three distinct modes are possible:

(i) Ion beam milling alone with an inert gas: in this mode the invention functions as a conventional ion beam milling system. It may be used on a whole range of metallic, ceramic and semiconductor materials. However, the new specimen holder permits very low milling angles which considerably reduces ion beam damage of the specimen.

(ii) beam milling with an inert gas in combination with molecular gas jetting: this mode is suited to the preparation of III-V and II-VI compound semiconductors and their alloys. It especially effective on InP, CdTe and alloys containing indium, cadmium or mercury for which conventional ion beam milling results in the creation of crystal imperfections and metallic islands on the surface. Formation of these islands is prevented by exposure of the specimen to an iodine or bromine molecular gas jet. The reaction rate between the iodine or bromine and the metallic island is maximized by the specimen holder heater. The combined mode may also be used to effect with a range of specimen materials and a variety of gas sources. For example, the thinning rate of tungsten is considerably increased by combined ion beam/molecular gas jet milling.

(iii) Molecular gas jetting along: even with the extremely low milling angles possible with the new specimen holder, some ion beam damage is introduced into the specimen. This is apparent as a thin amorphous layer, which obscures the underlying crystalline specimen, preventing good atomic resolution TEM. Molecular gas jetting alone removes this final artefact.

DESCRIPTION OF AN ALTERNATIVE EMBODIMENT

Figure 2:
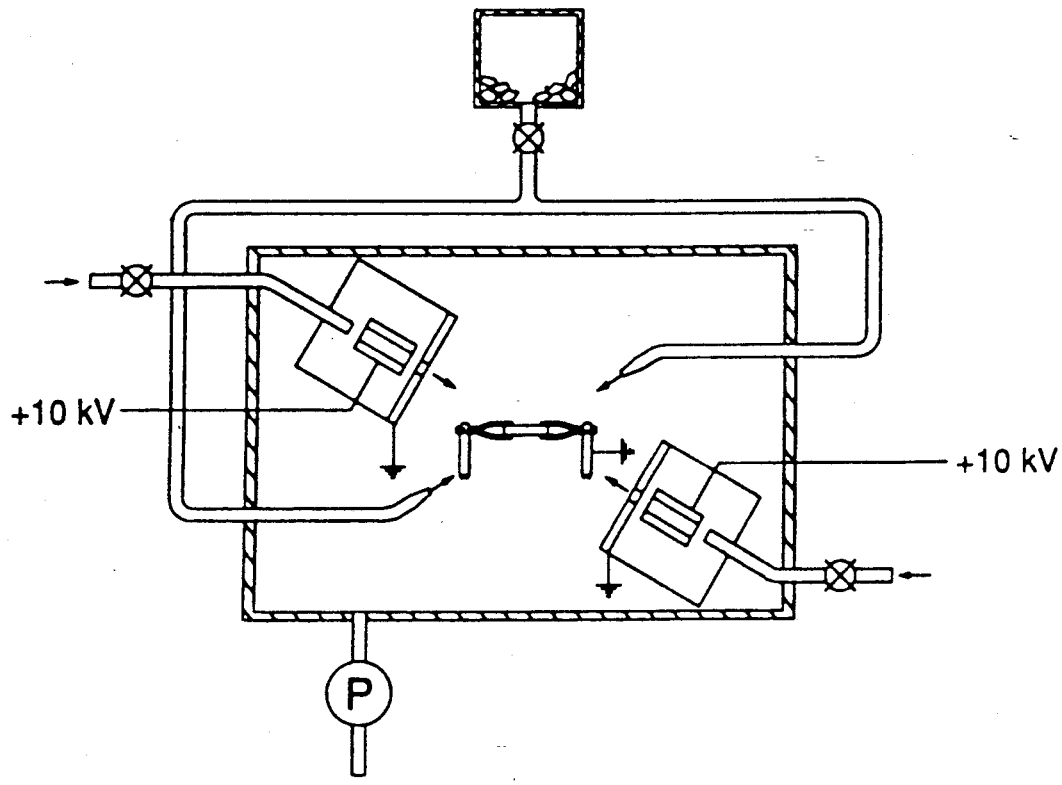
FIG. 2 illustrates an alternative embodiment of the invention utilizing a standard specimen holder.

FIG. 2 illustrates an alternative embodiment of the invention. This shows a conventional arrangement of ion guns and specimen holder, permitting milling from both sides of the specimen with the addition of a bifurcated molecular gas jet with nozzles directed at each side of the specimen. This embodiment has many of the disadvantages of prior art systems. In particular, the method of mounting the specimen limits the milling angle to a minimum of ~10° and promotes contamination of the specimen from material sputtered from the specimen holder. Further, the holder design makes it difficult to position the molecular gas jet nozzles sufficiently close to the specimen to enjoy the maximum benefit of the reactive process. However, this configuration is suitable for modifying existing ion beam milling systems so that they can also enjoy some of the benefits of the present invention.

SUMMARY, RAMIFICATIONS AND SCOPE

Accordingly, the reader will see that not only can the invention prepare high quality TEM specimens from compound semiconductors by a molecular gas jet in combination with ion beam milling but that other modes are possible. For example, the invention can be operated as a conventional ion beam milling system alone or it may be operated in a molecular gas jetting mode alone. Further additional advantages include:

(i) a reduction in the quantities of corrosive and toxic material used, thereby extending the lifetime of system components, a reduction which is particularly great if most of the milling is undertaken by the conventional ion beam milling mode alone and the molecular gas jet used for only final removal of surface artefacts;

(ii) a reduction in the contamination of the specimen;

(iii) a reduction in ion beam damage by permitting grazing incidence ion beam milling;

(iv) increased efficiency in the removal of the volatile compounds created from reaction with the iodine or bromine jet by heating the specimen.

While the above description contains many specificities, these should not be construed as limitations on the scope of the invention but merely as exemplifications of the preferred embodiments thereof. Those skilled in the art will envisage other possible variations within its scope. For example, the invention need not be limited to a single molecular gas jet and significant advantages could be obtained with several jets, each using a different gas. Similarly, the reduced milling rate arising from the very low milling angle can be compensated for with more than two ion guns. It will also be obvious to those skilled in the art to add a heater to capsule 46 to increase the flow of vapor into vacuum chamber 14. This improvement would also increase the variety of chemicals which may sublimated or evaporated to produce a vapor for injection into vacuum chamber 14.

Thus the scope of the invention should be determined by the appended claims and their legal equivalents, rather than by the examples given.

What is claimed is:

1. A method for the preparation of high quality specimens free from artefacts and suitable for high resolution transmission electron microscopy comprising the steps of:
   (i) mounting a specimen in a vacuum chamber,
   (ii) directing at the specimen an energetic, unfocused beam of ions neutrals, and
   (iii) simultaneously directing at the specimen a separate, independent low energy molecular beam, said specimen being positioned such that the angle between the specimen surface and said energetic ion beam is between 0° and 10°, whereby said specimens may be thinned to electron transparency without the production of thinning artefacts.

2. Apparatus for the preparation of high quality specimens free from artefacts and suitable for high resolution transmission electron microscopy comprising:
   (i) a vacuum chamber,
   (ii) a pump for maintaining a vacuum within the chamber,
   (iii) a high voltage supply,
   (iv) a holder inside the chamber for holding the specimen,
   (v) a plurality of ion beam guns directing at the specimen an energetic beam of ions and neutrals generated by high voltage discharge through a gas, and
   (vi) a nozzle adjacent to the specimen, said nozzle directing at the specimen a low energy molecular beam, said specimen being positioned such that the angle between the specimen surface and said energetic ion beam is between 0° and 10°, whereby said specimens may be thinned to electron transparency without the production of thinning artefacts.

3. The apparatus of claim 2 wherein said holder comprises
   (i) a pedestal, and
   (ii) specimen securing means, whereby said specimen may be securely seated on the top face of said pedestal, so permitting an ion beam to be directed at the specimen with an angle of between 0° and 10° between said ion beam and the specimen surface without any shadowing of the specimen by said specimen holder.

4. The apparatus of claim 3 wherein said securing means comprise a raised lip on the top surface of said pedestal.

5. A specimen holder for ion beam thinning systems comprising
   (i) a pedestal, and
   (ii) specimen securing means, whereby said specimen may be securely seated on the top face of said pedestal, so permitting an ion beam to be directed at the specimen with an angle of between 0° and 10° between said ion beam and the specimen surface without any shadowing of the specimen by said specimen holder.

6. The apparatus of claim 5 wherein said securing means comprise a raised lip on the top surface of said pedestal.

7. A method for the preparation of high quality specimens free from artefacts and suitable for high resolution transmission electron microscopy comprising the steps of:
   (i) mounting a specimen in a vacuum chamber, and
   (ii) directing at the specimen an energetic, unfocused beam of ions and neutrals, said specimen being positioned such that the angle between the specimen surface and said energetic ion beam is between 0° and 10°, whereby said specimens may be thinned to electron transparency without the production of thinning artefacts.

8. Apparatus for the preparation of high quality specimens free from artefacts and suitable for high resolution transmission electron microscopy comprising:
   (i) a vacuum chamber,
   (ii) a pump for maintaining a vacuum within the chamber,
   (iii) a high voltage supply,
   (iv) a holder inside the chamber for holding the specimen, and
   (v) a plurality of ion beam guns directing at the specimen an energetic beam of ions and neutrals generated by high voltage discharge through a gas, said specimen being positioned such that the angle between the specimen surface and said energetic ion beam is between 0° and 10°, whereby said specimens may be thinned to electron transparency without the production of thinning artefacts.

9. The apparatus of claim 8 wherein said holder comprises
   (i) a pedestal, and
   (ii) specimen securing means, whereby said specimen may be securely seated on the top face of said pedestal, so permitting an ion beam to be directed at the specimen with an angle of between 0° and 10° between said ion beam and the specimen surface without any shadowing of the specimen by said specimen holder.

10. The apparatus of claim 9 wherein said securing means comprise a raised lip on the top surface of said pedestal.

* * * * *